US011774001B2

(12) United States Patent
Govari et al.

(10) Patent No.: US 11,774,001 B2
(45) Date of Patent: Oct. 3, 2023

(54) SOLENOID VALVE SHOCK ABSORBER

(71) Applicant: JOHNSON & JOHNSON SURGICAL VISION, INC., Irvine, CA (US)

(72) Inventors: Assaf Govari, Haifa (IL); Yehuda Algawi, Binyamina (IL); Eran Aharon, Haifa (IL); Ilya Sitnitsky, Nahariya (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 346 days.

(21) Appl. No.: 17/240,505

(22) Filed: Apr. 26, 2021

(65) Prior Publication Data
US 2022/0341505 A1    Oct. 27, 2022

(51) Int. Cl.
*F16K 31/06* (2006.01)
*A61F 9/007* (2006.01)
(Continued)

(52) U.S. Cl.
CPC ...... *F16K 31/0668* (2013.01); *A61F 9/00745* (2013.01); *F16K 3/314* (2013.01);
(Continued)

(58) Field of Classification Search
CPC .. F16K 31/0668; F16K 3/314; F16K 31/0648; F16K 31/0658; F16K 31/0686;
(Continued)

(56) References Cited

U.S. PATENT DOCUMENTS 2,884,196 A * 4/1959 Allen .................. B60H 1/2212
126/116 A
3,023,777 A * 3/1962 Collins .............. F16K 31/0606
251/332
(Continued)

FOREIGN PATENT DOCUMENTS

DE          20318275 U1    2/2004
EP          0997363 A2     5/2000
(Continued)

*Primary Examiner* — Shaun L David
*Assistant Examiner* — Rachael L Geiger
(74) *Attorney, Agent, or Firm* — JOHNSON & JOHNSON SURGICAL VISION, INC.

(57) ABSTRACT

In one embodiment, a fluid dynamics system includes a solenoid valve including a valve body including ports including an inlet and outlet port, and a valve cavity having a direction of elongation and configured to provide fluid connectivity between ones of the ports, a solenoid coil disposed around valve cavity, and a plunger including a permanent magnet, and configured to move back-and-forth along the direction of elongation between a first and a second position in the valve cavity selectively controlling the fluid connectivity between respective ones of the ports, the valve body including shock absorber(s) to soften striking of the plunger against the valve body in the direction of elongation, and a controller configured to apply at least one current to the solenoid coil to selectively move the plunger between the first and second position, and to selectively maintain the plunger in the first position and the second position.

28 Claims, 9 Drawing Sheets

(51) Int. Cl.
*F16K 3/314* (2006.01)
*F16F 1/36* (2006.01)

(52) U.S. Cl.
CPC ... *A61B 2217/005* (2013.01); *A61B 2217/007* (2013.01); *F16F 1/3605* (2013.01); *F16F 2224/025* (2013.01)

(58) Field of Classification Search
CPC .. F16K 31/082; F16K 31/084; F16K 31/0651; F16K 31/0675; A61F 9/00–08; A61F 2/14–18; A61B 2217/005; A61B 2217/007; F16F 1/3605; F16F 2224/025
See application file for complete search history.

(56) References Cited

U.S. PATENT DOCUMENTS

| | | | | |
|---|---|---|---|---|
| 3,202,182 A | * | 8/1965 | Haviland | F02D 13/04 251/282 |
| 3,530,943 A | * | 9/1970 | Taylor | A01B 15/20 172/667 |
| 4,205,593 A | * | 6/1980 | Sakakibara | F02D 31/007 335/277 |
| 4,326,438 A | * | 4/1982 | Ballerstein | B23D 45/12 82/53.1 |
| 4,991,957 A | * | 2/1991 | Sakamoto | A61B 1/009 356/241.4 |
| 5,011,113 A | * | 4/1991 | Stobbs | F16F 9/46 251/129.21 |
| 2004/0113113 A1 | | 6/2004 | Krimmer et al. | |
| 2008/0312594 A1 | | 12/2008 | Urich et al. | |
| 2009/0159823 A1 | | 6/2009 | Matsunaga et al. | |
| 2013/0053764 A1 | | 2/2013 | Jaeger-Waldau | |
| 2013/0267919 A1 | | 10/2013 | Caso et al. | |
| 2013/0267933 A1 | | 10/2013 | Felber | |
| 2014/0030149 A1 | | 1/2014 | Takeuchi | |
| 2014/0276498 A1 | | 9/2014 | Connor et al. | |
| 2015/0332834 A1 | | 11/2015 | Schudt | |
| 2019/0247050 A1 | | 8/2019 | Goldsmith | |
| 2020/0107958 A1 | | 4/2020 | Wong et al. | |
| 2020/0179169 A1 | * | 6/2020 | Agahi | H01F 7/064 |
| 2021/0220164 A1 | * | 7/2021 | Kim | A61F 7/00 |

FOREIGN PATENT DOCUMENTS

| | | |
|---|---|---|
| JP | 2003225247 A | 8/2003 |
| WO | 2010124755 A1 | 11/2010 |
| WO | WO-2019209081 A1 * 10/2019 ......... A61B 18/0218 |

* cited by examiner

SOLENOID VALVE SHOCK ABSORBER

FIELD OF THE INVENTION

The present invention relates to medical systems, and in particular, but not exclusively to, fluid dynamics in medical systems.

BACKGROUND

A cataract is a clouding and hardening of the eye's natural lens, a structure which is positioned behind the cornea, iris and pupil. The lens is mostly made up of water and proteins and as people age these proteins change and may begin to clump together obscuring portions of the lens. To correct this, a physician may recommend phacoemulsification cataract surgery. In the procedure, the surgeon makes a small incision in the sclera or cornea of the eye. Then a portion of the anterior surface of the lens capsule is removed to gain access to the cataract. The surgeon then uses a phacoemulsification probe, which has an ultrasonic handpiece with a needle. The tip of the needle vibrates at ultrasonic frequency to sculpt and emulsify the cataract while a pump aspirates particles and fluid from the eye through the tip. Aspirated fluids are replaced with irrigation of a balanced salt solution (BSS) to maintain the anterior chamber of the eye. After removing the cataract with phacoemulsification, the softer outer lens cortex is removed with suction. An intraocular lens (IOL) is then introduced into the empty lens capsule restoring the patient's vision.

SUMMARY

There is provided in accordance with an embodiment of the present disclosure, a fluid dynamics system, including a solenoid valve including a valve body including ports including an inlet port and an outlet port, a valve cavity having a direction of elongation and configured to provide fluid connectivity between respective ones of the ports, and at least one shock absorber, a solenoid coil disposed in the valve body around the valve cavity, and a plunger including a permanent magnet, and configured to move back-and-forth along the direction of elongation between a first position and a second position in the valve cavity to selectively control the fluid connectivity between respective ones of the ports, wherein the at least one shock absorber is configured to soften striking of the plunger against the valve body in the direction of elongation, and a controller configured to apply at least one current to the solenoid coil to selectively move the plunger between the first position and the second position, and to selectively maintain the plunger in the first position and the second position.

Further in accordance with an embodiment of the present disclosure the plunger does not have a fixed rest position in the valve cavity.

Still further in accordance with an embodiment of the present disclosure the plunger does not include a restoring element configured to restore the plunger to a fixed rest position.

Additionally, in accordance with an embodiment of the present disclosure the plunger will not remain in the first position and second position without applying the at least one current to the solenoid coil.

Moreover, in accordance with an embodiment of the present disclosure the plunger will remain in the first position or the second position upon application of the at least one current to the solenoid coil.

Further in accordance with an embodiment of the present disclosure the valve body includes a first shock absorber and a second shock absorber configured to soften striking of the plunger against the valve body in the direction of elongation when the plunger strikes the valve body at the first position, and when the plunger strikes the valve body at the second position, respectively.

Still further in accordance with an embodiment of the present disclosure the first shock absorber and the second shock absorber do not include a spring.

Additionally, in accordance with an embodiment of the present disclosure the first shock absorber and the second shock absorber each include resilient material.

Moreover, in accordance with an embodiment of the present disclosure the resilient material includes one or more selected from the group consisting of silicone rubber, synthetic rubber, natural rubber, and polyurethane.

Further in accordance with an embodiment of the present disclosure the first shock absorber and the second shock absorber each include a flat surface facing the plunger.

Still further in accordance with an embodiment of the present disclosure the first shock absorber and the second shock absorber each include a rounded surface facing the plunger.

Additionally, in accordance with an embodiment of the present disclosure the first shock absorber and the second shock absorber each include a conical surface facing the plunger.

Moreover, in accordance with an embodiment of the present disclosure the controller is configured to apply a first current to the solenoid coil to activate the solenoid coil with a first polarity to cause the plunger to move and be maintained in the first position, and apply a second current to the solenoid coil to activate the solenoid coil with a second opposite polarity to cause the plunger to move and be maintained in the second position.

Further in accordance with an embodiment of the present disclosure the permanent magnet has a center with respect to the direction of elongation, the solenoid coil has a center with respect to the direction of elongation, and the valve body further includes a spacer coupled with the first shock absorber, to prevent the center of the magnet from moving in the direction of elongation past the center of the solenoid coil and maintain asymmetry between the center of the solenoid coil and the center of the permanent magnet with respect to the direction of elongation.

Still further in accordance with an embodiment of the present disclosure in the first position of the plunger, the plunger abuts the first shock absorber.

Additionally in accordance with an embodiment of the present disclosure, the system includes a medical tool including the solenoid valve, an irrigation channel, an aspiration channel which traverses the solenoid valve, and a sensor configured to provide a signal indicative of a fluid metric in the aspiration channel, the controller being configured to selectively control the fluid connectivity in the aspiration channel between the inlet port and the outlet port responsively to the fluid metric.

Moreover, in accordance with an embodiment of the present disclosure the fluid metric is a pressure level.

Further in accordance with an embodiment of the present disclosure the controller is configured to detect a rate of change of the fluid metric in the aspiration channel, and reduce the fluid connectivity between the inlet port and the outlet port responsively to the detected rate of change passing a given rate of change.

Still further in accordance with an embodiment of the present disclosure the controller is configured to increase the fluid connectivity between the inlet port and the outlet port responsively to the fluid metric passing a given value.

Additionally, in accordance with an embodiment of the present disclosure the medical tool further includes a probe body including a horn, a needle, a part of the irrigation channel and a section of the aspiration channel, and a fluid dynamics cartridge configured to be reversibly connected to the probe body, and including the sensor and the solenoid valve, which includes another section of the aspiration channel.

Moreover, in accordance with an embodiment of the present disclosure the fluid dynamics cartridge includes the controller.

There is also provided in accordance with another embodiment of the present disclosure, a fluid dynamics system, including a solenoid valve including a valve body including ports including an inlet port and an outlet port, a valve cavity having a direction of elongation and configured to provide fluid connectivity between respective ones of the ports, and at least one shock absorber, a solenoid coil disposed in the valve body around the valve cavity, and a plunger including magnetic material, and configured to move back-and-forth along the direction of elongation between a first position and a second position in the valve cavity to selectively control the fluid connectivity between respective ones of the ports, wherein the at least one shock absorber is configured to soften striking of the plunger against the valve body in the direction of elongation, wherein the at least one shock absorber includes a conical surface facing the plunger.

Further in accordance with an embodiment of the present disclosure the plunger does not have a fixed rest position in the valve cavity.

Still further in accordance with an embodiment of the present disclosure the plunger does not include a restoring element configured to restore the plunger to a fixed rest position.

Additionally, in accordance with an embodiment of the present disclosure the plunger will not remain in the first position and second position without applying at least one current to the solenoid coil.

Moreover, in accordance with an embodiment of the present disclosure the plunger will remain in the first position or the second position upon application of at least one current to the solenoid coil.

Further in accordance with an embodiment of the present disclosure the valve body includes a first shock absorber and a second shock absorber configured to soften striking of the plunger against the valve body in the direction of elongation when the plunger strikes the valve body at the first position, and when the plunger strikes the valve body at the second position, respectively.

Still further in accordance with an embodiment of the present disclosure the first shock absorber and the second shock absorber do not include a spring.

Additionally, in accordance with an embodiment of the present disclosure the first shock absorber and the second shock absorber each include resilient material.

Moreover, in accordance with an embodiment of the present disclosure the resilient material includes one or more selected from the group consisting of silicone rubber, synthetic rubber, natural rubber, and polyurethane.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
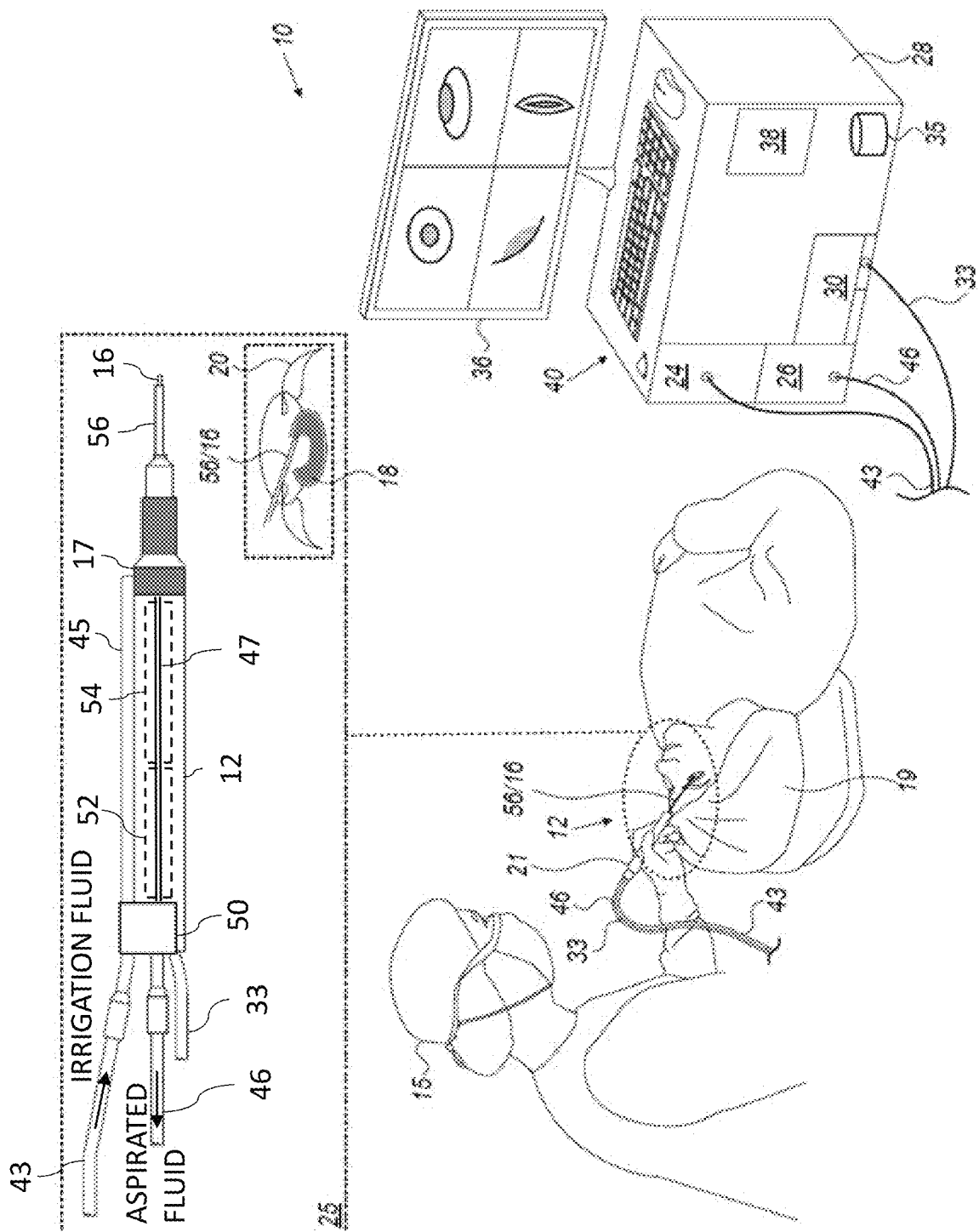
FIG. 1 is a partly pictorial, partly block diagram view of a phacoemulsification system constructed and operative in accordance with an embodiment of the present invention.

During phacoemulsification of an eye lens, the emulsified lens particles are aspirated. When a particle blocks the inlet of an aspiration channel (which could be in a needle of a phacoemulsification probe) causing occlusion of the channel, the vacuum in the channel increases. When the channel becomes unblocked (e.g., by the particle being subsequently sucked down the channel), the high vacuum in the channel causes an aspiration surge known as a post occlusion surge, which may have traumatic consequences to the eye. For example, sensitive parts of the eye may be damaged or come into contact with the needle of the phacoemulsification probe.

A possible solution to the problem of vacuum level surge is incorporating an aspiration bypass. Such a bypass may consist of a small hole or channel between an irrigation channel of the probe and the aspiration channel. When a blockage occurs, the high vacuum diverts irrigation fluid into the aspiration channel via the hole, thereby limiting the vacuum level.

However, the above-described bypass aspiration technique is still prone to produce a traumatic aspiration surge when the channel unblocks, since the high vacuum is present in a long tube (which being flexible may also be compressed adding to the vacuum problem) between a portion of the aspiration channel inside the emulsification probe and the aspiration pump, and that large, partially vacant volume, may therefore cause a surge when the occlusion breaks. Moreover, diversion of irrigation fluid may cause an uncontrolled pressure-drop in the irrigation channel, which may also pose a risk to the eye.

Embodiments of the present invention generally solve the above problems by removing or reducing the pressure difference in the aspiration channel during the occlusion clearance. Embodiments of the present invention control fluid connectivity in the aspiration channel during occlusion clearance using an extremely fast-acting and programmable solenoid valve. The solenoid valve includes a solenoid coil which moves a plunger including a permanent magnet in a valve cavity. Two parts of the aspiration channel are connected to the valve cavity via ports in the valve cavity.

Therefore, movement of the plunger in the valve cavity controls the fluid connectivity in the aspiration channel.

In some embodiments, the permanent magnet may be replaced by any suitable magnetic material, which is subjected to a force in a magnetic field, for example, but not limited to, iron, cobalt, nickel, gadolinium, and/or neodymium.

The solenoid valve does not need a restoring element (such as a spring) to keep the plunger in a rest position when a current is not applied to the solenoid coil. An electric current needs to be applied to the solenoid coil to selectively open the valve and keep the valve open, and to close the valve and keep the valve closed. If a current is not supplied to the solenoid coil, the position of the plunger may be unstable and unknown. Using a solenoid valve without a restoring element allows the plunger to be moved quickly with a selected force, while minimizing electrical power needed to open or close the valve thereby reducing heat generated by the solenoid valve. The solenoid valve is opened and closed by changing the polarity of the solenoid coil by changing the direction of the current applied to the solenoid coil.

In some embodiments, a spacer is placed in the path of the plunger preventing a center of the permanent magnet of the plunger (with respect to a direction of elongation of the valve cavity) from being aligned with a center of the solenoid coil (with respect to a direction of elongation of the valve cavity). In this asymmetrical state, the permanent magnet is not subjected to unstable forces from the solenoid coil and the plunger can be moved from one position to another by changing the polarity of the solenoid coil thereby providing a quick and effective opening and closing of the solenoid valve.

As the opening and closing of the solenoid valve is performed quickly and sometimes the solenoid valve is repeatedly opened and closed many times a second, the plunger may strike against a body of the valve causing a loud noise and vibration of a medical tool (such as a phacoemulsification probe) in which the valve is operating. The noise and vibration are disturbing for the physician operating the tool as well as making it difficult for the physician to steadily hold the tool. Therefore, in some embodiments, the solenoid valve includes one or more shock absorbers to soften the striking of the plunger against the valve body in the direction of elongation. The solenoid valve may include two shock absorbers placed at either end of the valve cavity to soften the striking of the plunger against the valve body as the plunger moves from one extreme to another within the valve cavity. The shock absorbers do not typically include springs. The shock absorbers are generally formed from a resilient material such as silicone rubber, natural rubber, synthetic rubber, or polyurethane. The shock absorbers may have any suitable shape. The shock absorbers include a surface which faces the plunger in use. This surface may have any suitable shape, for example, a flat surface, a rounded surface, or a conical surface.

In some embodiments, a sensor (e.g., pressure sensor, flow sensor, or any suitable sensor) connected to or coupled with the aspiration channel provides a signal indicative of a fluid metric (e.g., pressure level) in the aspiration channel and a controller selectively controls fluid connectivity along the aspiration channel by applying a suitable current to the solenoid coil to selectively open or close the solenoid valve. In some embodiments, when the controller detects a rate of change in the fluid metric (e.g., pressure level) in the aspiration channel passing (e.g., exceeding) a given rate of change, which is indicative of an occlusion breaking, the controller reduces fluid connectivity in the aspiration channel by closing the solenoid valve quickly (for example, in 10 milliseconds or less) thereby isolating the eye from the vacuum created in a majority of the aspiration channel and/or aspiration line until the pressure in the aspiration channel and/or aspiration line returns to a desired and/or safe pressure. The pressure in the aspiration channel may be changed, in a non-time critical manner, by adjusting or stopping an aspiration pump acting on the aspiration channel and/or by externally venting the aspiration line, and/or any other suitable method. Once the fluid metric (e.g., pressure level) in the aspiration channel passes a given value (e.g., given pressure level), the controller reopens the solenoid valve without causing a vacuum surge which could damage the eye.

In some embodiments, in addition to being linear, the solenoid valve is small and may be produced at low-cost thereby allowing the valve to be disposed of after use. Therefore, in some embodiments, the valve does not need to withstand repeated sterilization. The valve may be housed in a cartridge which is reversibly connected to the phacoemulsification probe and aspiration and irrigation tubes. The cartridge may then be removed from the probe and tubes after use for cleaning or disposal.

In some embodiments, sensors (e.g., a pressure sensor for the aspiration channel and a pressure sensor for the irrigation channel) may be included in the cartridge). Including the sensors in the cartridge may provide higher sensitivity to local changes in fluid dynamics and provide a higher degree of control of the pressure in the eye.

In some embodiments, the controller is also included in the cartridge. Including the controller in the cartridge may allow the controller to be configured for the calibration of the solenoid valve. Additionally, or alternatively, including the controller in the cartridge allows the controller to be close to the sensor or sensors which may be providing analog signals that could degrade if the signals needed to travel over a cable to a remote console in which the controller may otherwise be installed.

System Description

Reference is now made to FIG. 1 is a partly pictorial, partly block diagram view of a phacoemulsification system 10 constructed and operative in accordance with an embodiment of the present invention.

The phacoemulsification system 10 comprises a phacoemulsification probe 12 (e.g., handpiece). In some embodiments, the phacoemulsification probe 12 may be replaced by any suitable medical tool. As seen in the pictorial view of phacoemulsification system 10, and in inset 25, phacoemulsification probe 12 comprises a needle 16, a probe body 17, and a coaxial irrigation sleeve 56 that at least partially surrounds needle 16 and creates a fluid pathway between the external wall of the needle and the internal wall of the irrigation sleeve, where needle 16 is hollow to provide an aspiration channel. Moreover, irrigation sleeve 56 may have one or more side ports at, or near, the distal end to allow irrigation fluid to flow towards the distal end of the phacoemulsification probe 12 through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, Calif., USA.

In the embodiment of FIG. 1, during the phacoemulsification procedure, a pumping sub-system 24 comprised in a console 28 pumps irrigation fluid from an irrigation reservoir (not shown) to the irrigation sleeve 56 to irrigate the eye 20. The irrigation fluid is pumped via an irrigation tubing line 43 running from the console 28 to an irrigation channel 45 of probe 12, the distal end of the irrigation channel 45 including the fluid pathway in the irrigation sleeve 56. The irrigation tubing line 43 is typically flexible and may be prone to collapsing during an occlusion of the needle 16. In another embodiment, the pumping sub-system 24 may be coupled or replaced with a gravity fed irrigation source such as a balanced salt solution (BSS) bottle/bag.

Eye fluid and waste matter (e.g., emulsified parts of the cataract) are aspirated via an aspiration channel 47, which extends from the hollow of needle 16 through the phacoemulsification probe 12, and then via an aspiration tubing line 46 to a collection receptacle in the console 28. The aspiration is affected by a pumping sub-system 26, also comprised in console 28.

System 10 may include a fluid dynamics cartridge 50 (which in an embodiment, may be removable), which may include one or more valves to regulate the flow of fluid in the irrigation channel 45 and/or aspiration channel 47 as well as sensors, described in more detail with reference to FIGS. 2A-6. Part of the irrigation channel 45 and the aspiration channel 47 is disposed in the probe body 17 and part is disposed in the cartridge 50.

Phacoemulsification probe 12 includes other elements, such as a piezoelectric crystal 52 coupled to a horn 54 to drive vibration of needle 16. The piezoelectric crystal is configured to vibrate needle 16 in a resonant vibration mode. The vibration of needle 16 is used to break a cataract into small pieces during a phacoemulsification procedure. Console 28 comprises a piezoelectric drive module 30, coupled with the piezoelectric crystal 52, using electrical wiring running in a cable 33. Drive module 30 is controlled by a controller 38 and conveys processor-controlled driving signals via cable 33 to, for example, maintain needle 16 at maximal vibration amplitude. The drive module may be realized in hardware or software, for example, in a proportional-integral-derivative (PID) control architecture. The controller 38 may also be configured to receive signals from sensors in the phacoemulsification probe 12 and control one or more valves to regulate the flow of fluid in the irrigation channel 45 and/or the aspiration channel 47, as described in more detail with reference to FIG. 6. In some embodiments, at least some of the functionality of the controller 38 may be implemented using a controller disposed in the phacoemulsification probe 12 (e.g., the cartridge 50).

Controller 38 may receive user-based commands via a user interface 40, which may include setting a vibration mode and/or frequency of the piezoelectric crystal 52, and setting or adjusting an irrigation and/or aspiration rate of the pumping sub-systems 24/26. In some embodiments, user interface 40 and a display 36 may be combined as a single touch screen graphical user interface. In some embodiments, the physician 15 uses a foot pedal (not shown) as a means of control. Additionally, or alternatively, controller 38 may receive the user-based commands from controls located in a handle 21 of probe 12.

Some or all of the functions of controller 38 may be combined in a single physical component or, alternatively, implemented using multiple physical components. These physical components may comprise hard-wired or programmable devices, or a combination of the two. In some embodiments, at least some of the functions of controller 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements which are omitted for clarity of presentation. For example, physician 15 typically performs the procedure using a stereo microscope or magnifying glasses, neither of which are shown. Physician 15 may use other surgical tools in addition to probe 12, which are also not shown in order to maintain clarity and simplicity of presentation.

Figure 2A:
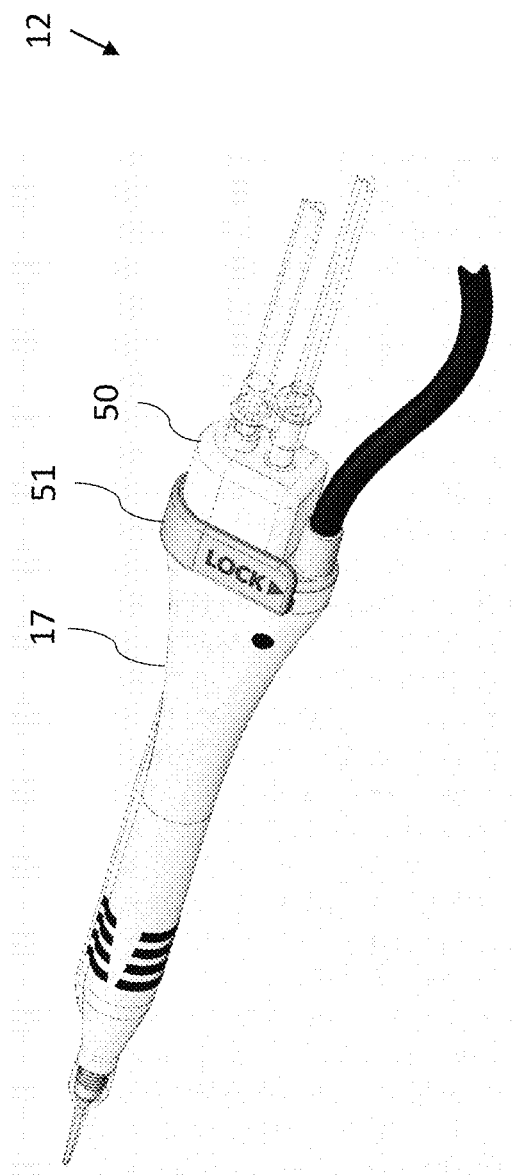
FIGS. 2A-B are views of a probe for use with the system of FIG. 1.
Figure 2B:
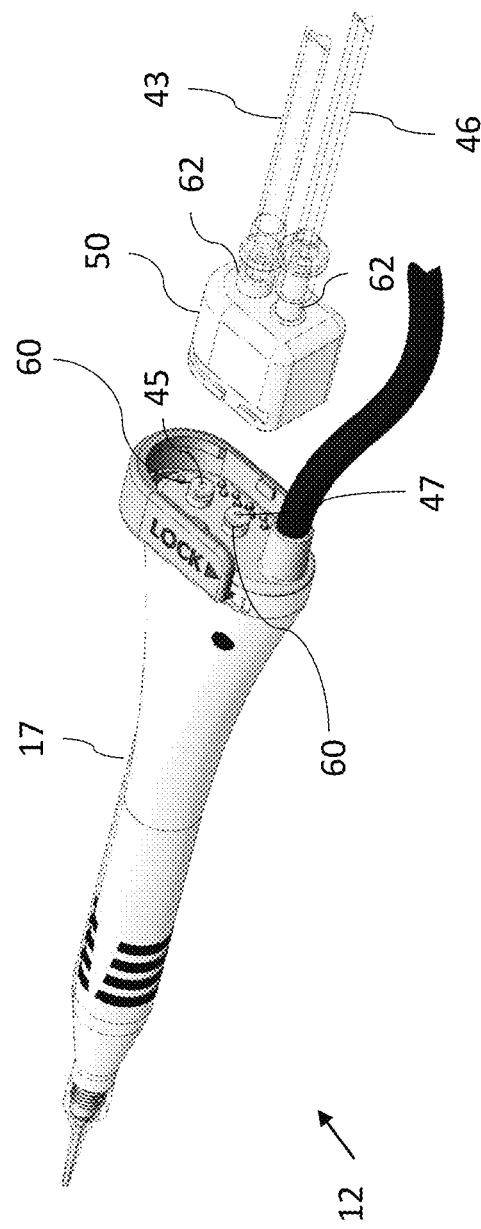

Reference is now made to FIGS. 2A-B, which are views of the phacoemulsification probe 12 for use with the system 10 of FIG. 1. FIG. 2A shows the cartridge 50, which is configured to be reversibly attached (using a clip 51) to the probe body 17 of the phacoemulsification probe 12. FIG. 2B shows the cartridge 50 detached from the probe body 17. FIG. 2B shows ports 60 of the irrigation channel 45 and the aspiration channel 47 on the probe body 17 for connecting with corresponding ports (not shown in FIG. 2B, but shown in FIG. 3A) of the cartridge 50. FIG. 2B also shows irrigation tubing line 43 and aspiration tubing line 46 connected to ports 62 of the cartridge 50.

Figure 3A:
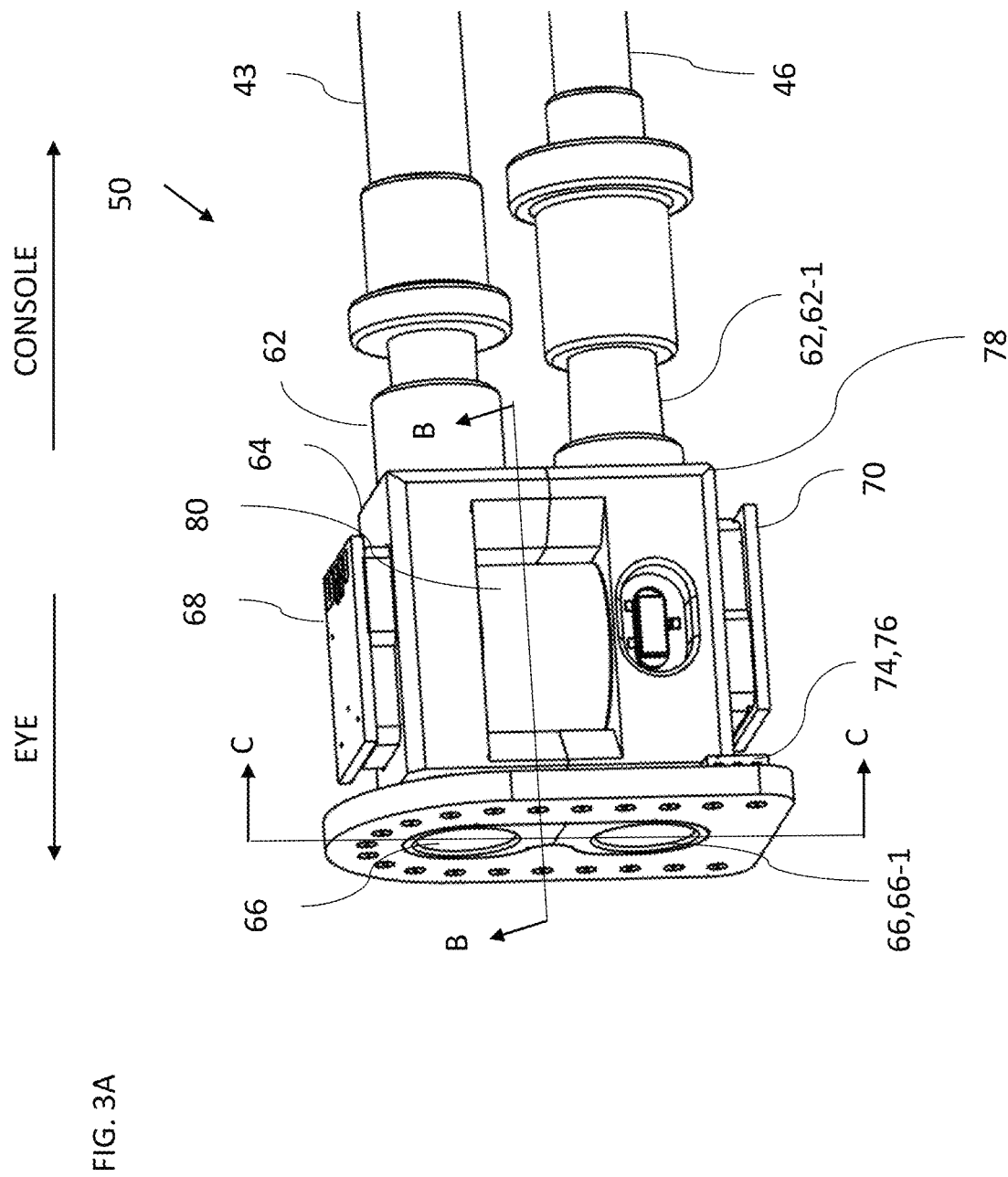
FIG. 3A is a schematic view of an interior of a fluid dynamics cartridge for use in the probe of FIGS. 2A-B.
Figure 3B:
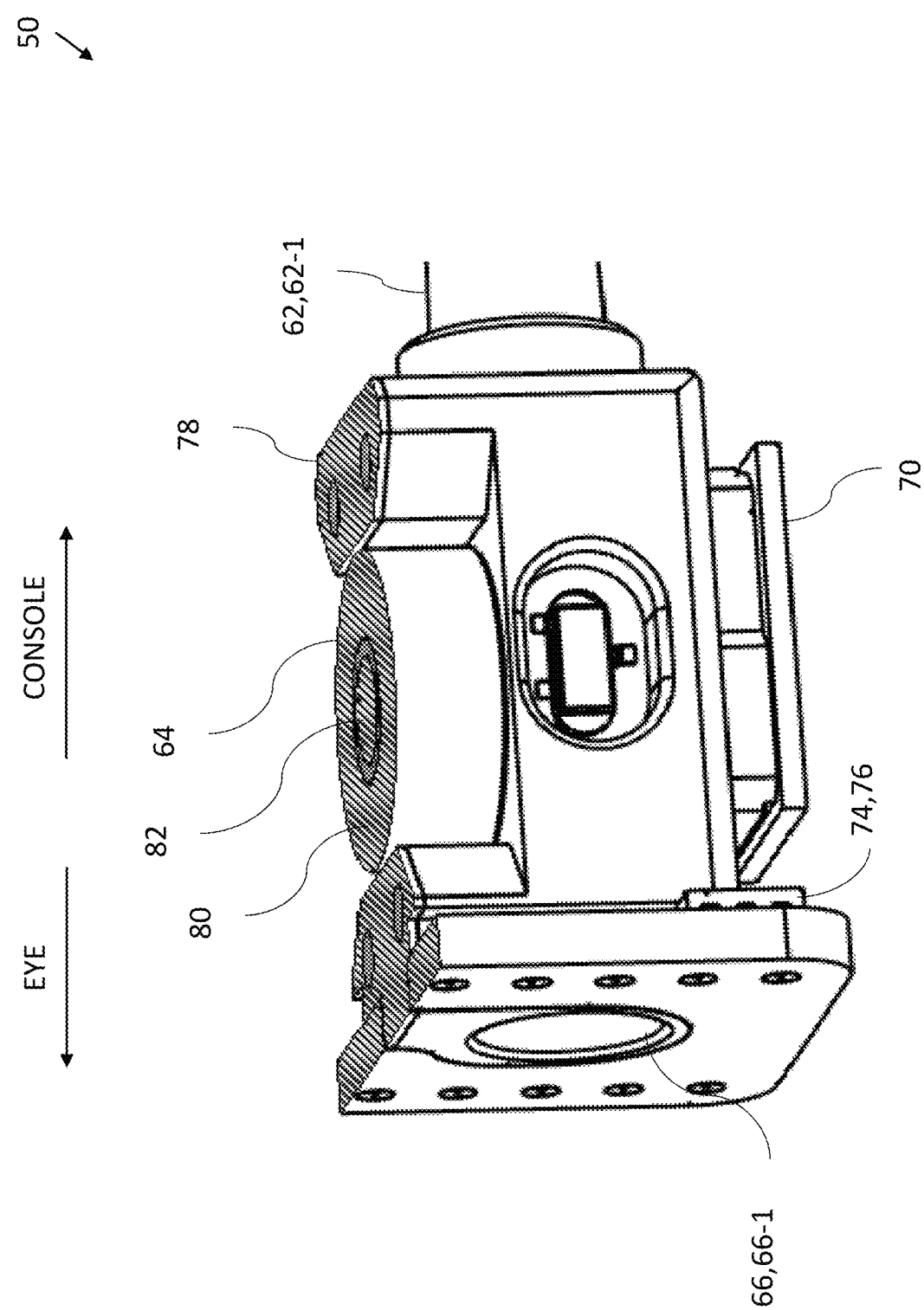
FIG. 3B is a cross-section of the fluid dynamics cartridge through line B:B of FIG. 3A.
Figure 3C:
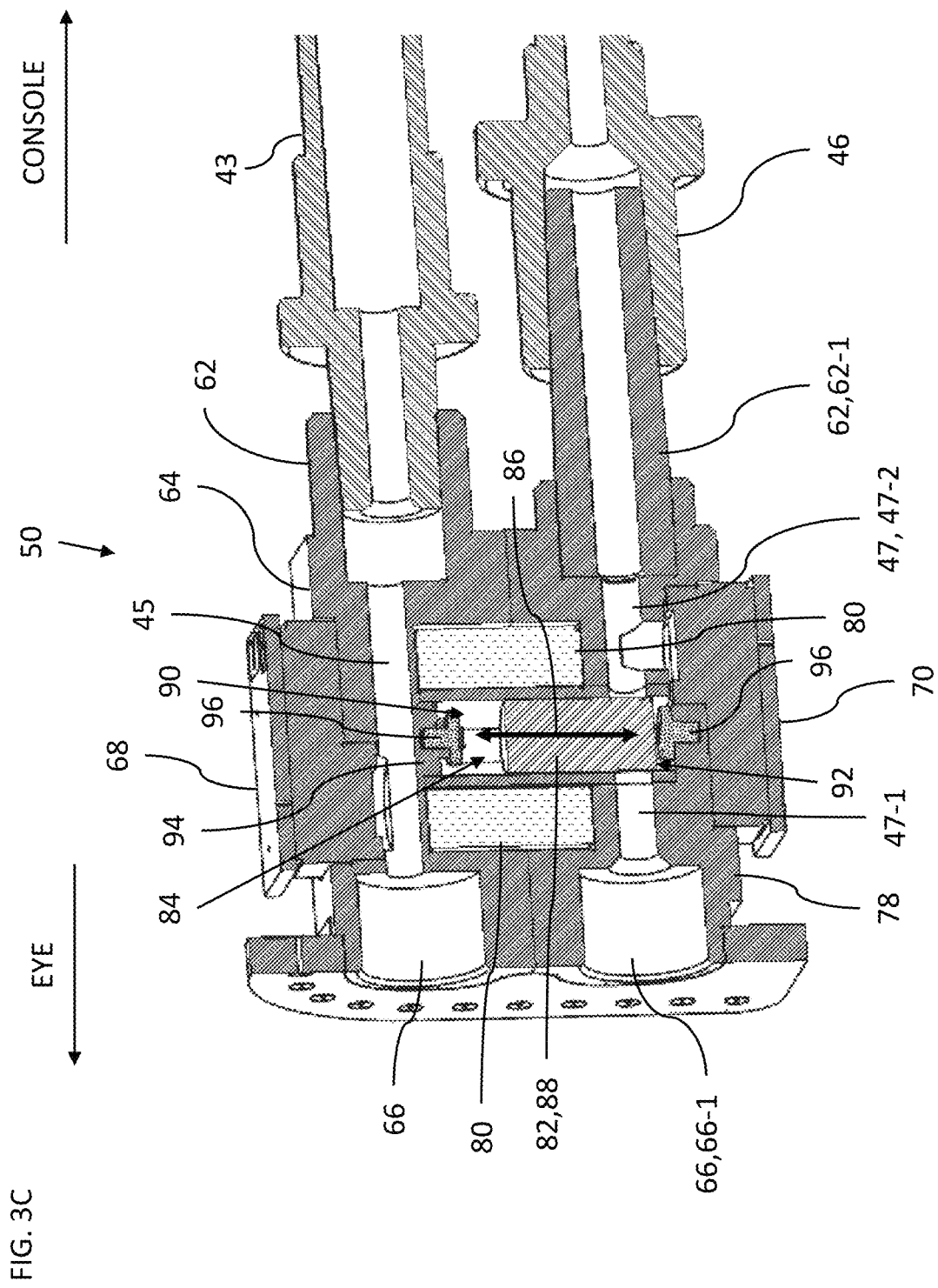
FIG. 3C is a cross-section of the fluid dynamics cartridge through line C:C of FIG. 3A.

Reference is now made to FIGS. 3A-C. FIG. 3A is a schematic view of an interior of a fluid dynamics cartridge 50 for use in the phacoemulsification probe 12 of FIGS. 2A-B. FIG. 3B is a cross-section of the fluid dynamics cartridge 50 through line B:B of FIG. 3A. FIG. 3C is a cross-section of the fluid dynamics cartridge 50 through line C:C of FIG. 3A.

The phacoemulsification probe 12 may include sensors 68, and 70 (which may be pressure sensors), and a solenoid valve 64. In some embodiments, the cartridge 50 includes: the solenoid valve 64, which includes ports 62 for connection to the irrigation tubing line 43 and aspiration tubing line 46, ports 66 for connection to the ports 60 (FIG. 2B), and sections of the irrigation channel 45 and aspiration channel 47; the sensor 68 connected to the irrigation channel 45; and the sensor 70 connected to aspiration channel 47 on the console 28 side of the solenoid valve 64 (as shown in FIG. 3C). The sensor 68 and the sensor 70 are configured to provide respective signals indicative of respective fluid metrics (e.g., pressure levels) in the irrigation channel 45 and in the aspiration channel 47. The aspiration channel 47 traverses the solenoid valve 64.

Including the sensors 68, 70 in the cartridge 50 may provide higher sensitivity to local changes in fluid dynamics and provide a higher degree of control of the pressure in the eye.

The phacoemulsification probe 12 may include a controller 74 to receive the signal(s) from the pressure sensor 68 and/or the pressure sensor 70, and control the fluid connectivity in the irrigation channel 45 and/or the aspiration channel 47 by selectively opening and closing the solenoid valve 64, responsively to the received signal(s). In some embodiments, the cartridge 50 may also include the controller 74 and/or a memory 76 (e.g., EEPROM) to hold calibration settings and/or a usage counter to count usage of the cartridge 50 and thereby prevent overuse of the cartridge 50. In some embodiments, the controller 74 may be included in the console 28 (FIG. 1). In some embodiments, the functionality of the controller 74 may be performed by the controller 38. Including the controller 74 in the cartridge 50 may allow the controller to be configured for the calibration of the solenoid valve 64. Additionally, or alternatively, including the controller 74 in the cartridge 50 allows the controller to be close to the sensors 68, 70 which may be providing analog signals that could degrade if the signals needed to travel over the cable 33 to the console 28 in which the controller 74 may otherwise be installed.

The cartridge 50 is compact and may be any suitable size. In some embodiments, the cartridge 50 may fit into a cube of 2.5 cm sides.

The aspiration channel 47 includes a section 47-1 coupled to an inlet port 66-1 and a section 47-2 coupled to an outlet port 62-1 (as shown in FIG. 3C). The controller 74 is configured to control the fluid connectivity in the aspiration channel 47 between the inlet port 66-1 and the outlet port 62-1 by selectively opening and closing the solenoid valve 64, responsively to the fluid metric (e.g., pressure level) in the aspiration channel 47. It should be noted that when the solenoid valve 64 is closed, the sensor 70 shown in FIG. 3C is configured to sense a fluid metric (e.g., pressure level) in the section 47-2 between the solenoid valve 64 and the console 28.

The solenoid valve 64 and its operation is now described in more detail. The solenoid valve 64 includes a valve body 78, a solenoid coil 80, and a plunger 82.

Reference is now made to FIG. 3C. The valve body 78 includes the ports 62, the ports 66, a valve cavity 84 having a direction of elongation 86 and configured to provide fluid connectivity between respective ones of the ports 62, 66 (e.g., between the inlet port 66-1 and outlet port 62-1). The solenoid coil 80 is disposed in the valve body 78 around valve cavity 84. The plunger 82 includes a permanent magnet 88. The permanent magnet 88 may comprise all of, or only part of, the plunger 82. For example, the plunger 82 may include the permanent magnet 88 coated or covered with a material of low friction. The plunger 82 is configured to move back-and-forth along the direction of elongation 86 between a position 90 and a position 92 in the valve cavity 84 selectively controlling the fluid connectivity between respective ones of the ports 62, 66 (e.g., between the inlet port 66-1 and outlet port 62-1). In some embodiments, the permanent magnet 88 may be replaced by any suitable magnetic material, which is subjected to a force in a magnetic field, for example, but not limited to, iron, cobalt, nickel, gadolinium, and/or neodymium.

The plunger 82 may have any suitable size, for example, a length in the range of 3 mm to 2 cm (e.g., 6 mm) and a diameter in the range of 1 mm to 1 cm (e.g., 3 mm). The valve body 78 may include a spacer 94 described in more detail with reference to FIGS. 5A-B below.

As the opening and closing of the solenoid valve 64 is performed quickly and sometimes the solenoid valve 64 is repeatedly opened and closed many times a second (as described in more detail with reference to FIG. 6), the plunger 82 may strike against the valve body 78 causing a loud noise and vibration of the phacoemulsification probe 12. The noise and vibration are disturbing for the physician 15 (FIG. 1) operating the phacoemulsification probe 12 as well as making it difficult for the physician 15 to steadily hold the phacoemulsification probe 12. Therefore, the solenoid valve 64 includes one or more shock absorbers 96 configured to soften the striking of the plunger 82 against the valve body 78 in the direction of elongation 86. The solenoid valve may include two shock absorbers 96 (as shown in FIG. 3C) placed at either end of the valve cavity 84 configured to soften the striking of the plunger 82 against the valve body 78 as the plunger 82 moves in the direction of elongation 86 from one extreme of the valve body 78 to another (e.g., from position 90 to position 92, and vice-versa) within the valve cavity 84. The shock absorbers 96 do not typically include springs. The shock absorbers 96 generally comprise, or are generally formed from, a resilient material such as silicone rubber, natural rubber, synthetic rubber, or polyurethane. In FIG. 3C, the upper shock absorber 96 forms part of the spacer 94.

The controller 74 (FIGS. 3A-B) is configured to apply at least one current to the solenoid coil 80 to selectively move the plunger 82 between the position 90 and the position 92, and to selectively maintain the plunger in the position 90 and the position 92, as described below in more detail with reference to FIGS. 5A-B.

Figure 3F:
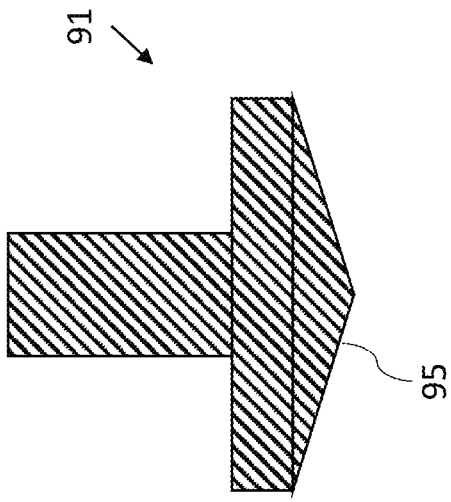
FIGS. 3F-G are cross-sectional views of alternative shock absorbers for use in the cartridge of FIG. 3C.
Figure 3G:
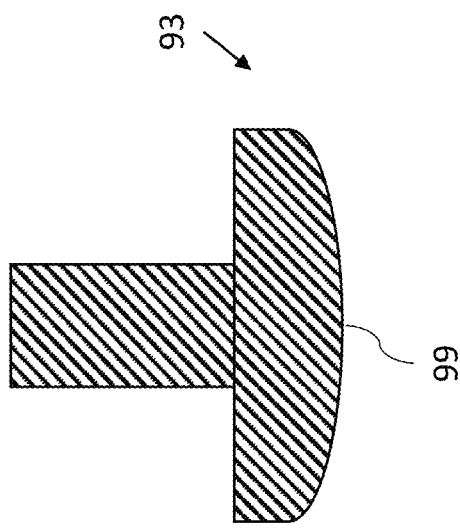
Figure 3D:
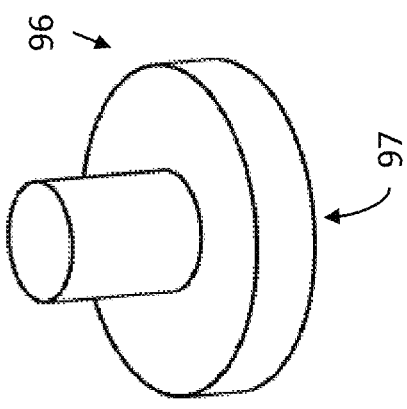
FIGS. 3D-E are schematic views of a shock absorber for use in the cartridge of FIG. 3C.
Figure 3E:
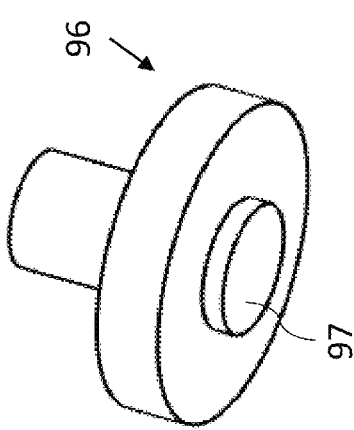

Reference is now made to FIGS. 3D-E, which are schematic views of the shock absorber 96 for use in the cartridge 50 of FIG. 3C. Each shock absorber 96 includes a flat surface 97 facing the plunger 82 (FIG. 3C).

Reference is now made to FIGS. 3F-G, which are cross-sectional views of alternative shock absorbers 91, 93 for use in the cartridge 50 of FIG. 3C. Two shock absorbers 91 or two shock absorber 93 (or any suitable combination) may be used in the solenoid valve 64 instead of the shock absorbers 96. The shock absorber 91 of FIG. 3F includes a conical surface 95 facing the plunger 82. The shock absorber 93 of FIG. 3G includes a rounded surface 99 facing the plunger 82.

Figure 4B:
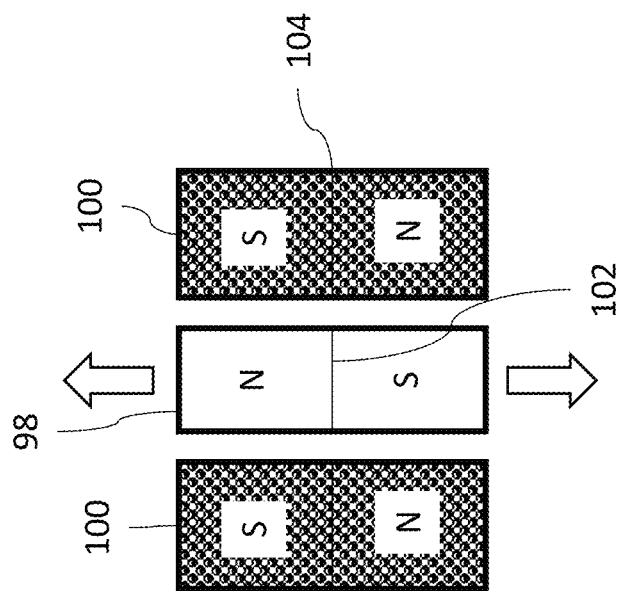
FIGS. 4A-B are schematic views of a permanent magnet in a solenoid coil.
Figure 4A:
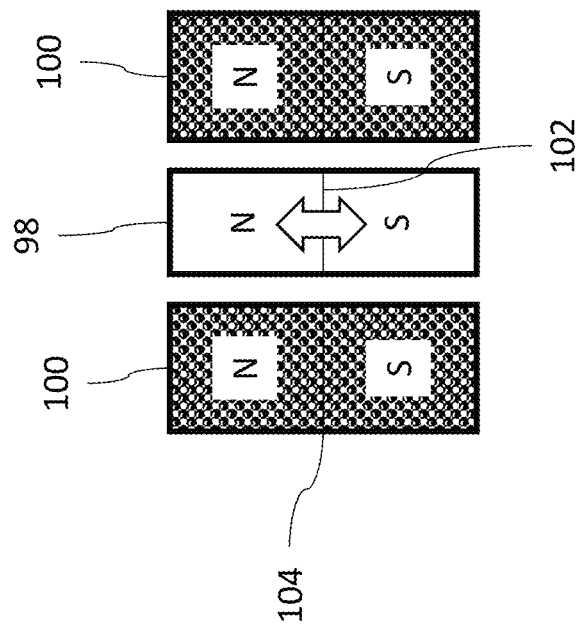

Reference is now made to FIGS. 4A-B, which are schematic views of a permanent magnet 98 in a solenoid coil 100.

In the configuration of FIG. 4A, the polarity of the solenoid coil 100 is in the same direction as the polarity of the permanent magnet 98. In such a configuration, if a center 102 of the permanent magnet 98 is moved a little away from a center 104 of the solenoid coil 100, the permanent magnet 98 will oscillate around the center 104 of the solenoid coil 100 until the permanent magnet 98 settles so that the center 102 of the permanent magnet 98 is aligned with the center 104 of the solenoid coil 100. The permanent magnet 98 therefore rests in a stable position with respect to the solenoid coil 100.

In the configuration of FIG. 4B, the polarity of the solenoid coil 100 is in the opposite direction to the polarity of the permanent magnet 98. In such a configuration, if the center 102 of the permanent magnet 98 is moved a little away from the center 104 of the solenoid coil 100, the permanent magnet 98 will continue to move in that direction. The permanent magnet 98 in FIG. 4B is therefore in an unstable position with respect to the solenoid coil 100.

Figure 5A:
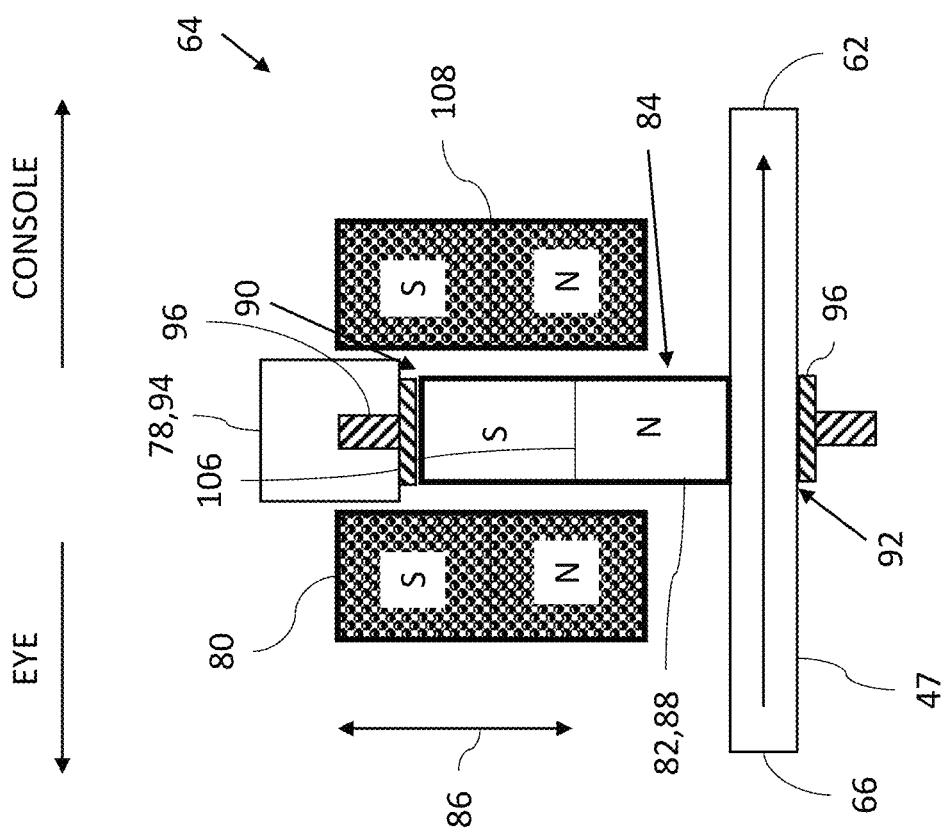
FIGS. 5A-B are schematic views of operation of a solenoid valve for use in the cartridge of FIGS. 3A-C.
Figure 5B:
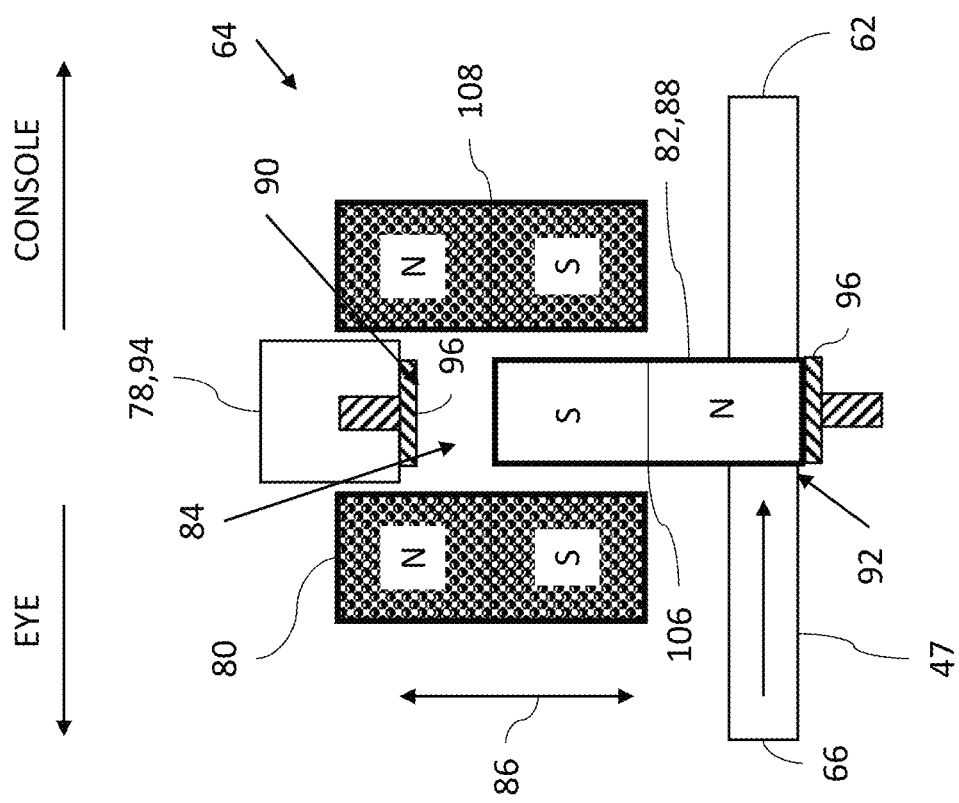

Reference is now made to FIGS. 5A-B, which are schematic views of operation of the solenoid valve 64 for use in the cartridge 50 of FIGS. 3A-C.

The plunger 82 is configured to move back-and-forth along the direction of elongation 86 between position 92 and position 90 in the valve cavity 84 selectively controlling the fluid connectivity between respective ones of the ports 66, 62. The controller 74 (FIGS. 3A-B) is configured to apply current to the solenoid coil 80 to selectively move the plunger 82 between the position 92 and position 90, and to selectively maintain the plunger in the position 92 and position 90. FIG. 5A shows the plunger 82 in position 92 blocking fluid connectivity in the aspiration channel 47. FIG. 5B shows the plunger 82 in position 90 allowing fluid connectivity in the aspiration channel 47.

The plunger 82 does not have a fixed rest position in the valve cavity 84. Even though in some orientations the plunger 82 may fall in one of the positions 92, 94 due to gravity, if the solenoid valve 64 is orientated differently the plunger 84 may fall to a different position. The plunger 82 does not include a restoring element (e.g., spring) configured to restore the plunger 82 to a fixed rest position. The plunger will not always remain in the position 92 or position 90 (e.g., if the orientation of the phacoemulsification probe 12 is changed) without applying current to the solenoid coil 80. In other words, for the solenoid valve 64 to function correctly, a current is applied to the solenoid coil 80 whether the solenoid valve 64 is to remain open or closed. The plunger 82 will remain in the position 90 or the position 92 upon application of current to the solenoid coil 80.

The controller 74 is configured to apply a current to the solenoid coil 80 to activate the solenoid coil 80 with a polarity to cause the plunger 82 to move and be maintained in the position 92 as shown in FIG. 5A. The controller 74 is configured to apply an opposite current to the solenoid coil 80 to activate the solenoid coil 80 with an opposite polarity to cause the plunger 82 to move and be maintained in the position 90 as shown in FIG. 5B.

The permanent magnet 88 has a center 106 with respect to the direction of elongation 86. The solenoid coil 80 has a center 108 with respect to the direction of elongation 86.

The valve body 78 includes the spacer 94 to prevent the center 106 of the magnet 88 moving in the direction of elongation 86 past the center 108 of the solenoid coil 80. Therefore, the spacer 94 maintains asymmetry between the center 108 of the solenoid coil 80 and the center 106 of the permanent magnet 88 with respect to the direction of elongation 86 so that the centers 106, 108 are never aligned with respect to the direction of elongation 86. The above asymmetry is desirable to allow movement of the permanent magnet 88 within the valve cavity 84 to be controlled and the maintained position of the permanent magnet 88 at the position 90 to be stable (as explained above with reference to FIGS. 4A-B). When plunger 82 is in position 90, plunger 82 abuts spacer 94 (see FIG. 5B).

The spacer 94 includes the upper shock absorber 96. When plunger 82 is in position 92, plunger 82 abuts the lower shock absorber 96, and when plunger 82 is in position 90, plunger 82 abuts the upper shock absorber 96. The upper and lower shock absorbers 96 are configured to soften striking of the plunger 82 against the valve body 78 in the direction of elongation 86 when the plunger 82 strikes the valve body 78 at position 90, and when the plunger 82 strikes the valve body 78 at position 92, respectively.

Figure 6:
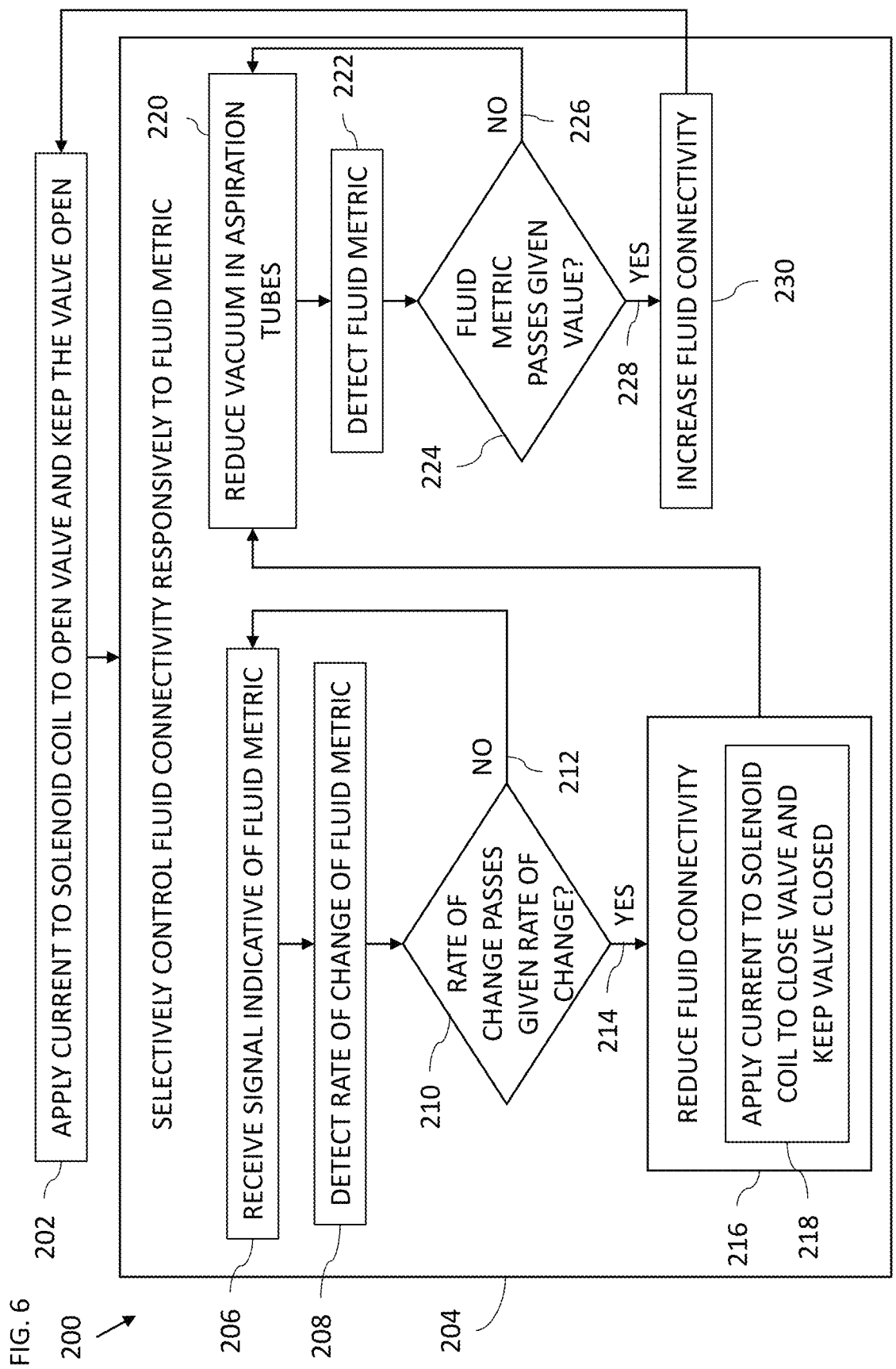
FIG. 6 is a flowchart including steps in a method of operation of system of FIG. 1.

Reference is now made to FIG. 6, which is a flowchart 200 including steps in an exemplary method of operation of system 10 of FIG. 1. Reference is also made to FIG. 3C.

The controller 74 is configured to apply (block 202) a current to the solenoid coil 80 to activate the solenoid coil 80 with a polarity to cause the plunger 82 to move and be maintained in the position 90 so that the solenoid valve 64 is open (and kept open) and there is fluid connectivity along the aspiration channel 47.

The controller 74 is configured to selectively control (block 204) the fluid connectivity responsively to a measured fluid metric (e.g., a sensed fluid flow or pressure level) in the phacoemulsification probe 12. In some embodiments, the controller 74 is configured to selectively control the fluid connectivity responsively to the fluid metric from the one or more sensors 68, 70 coupled with aspiration channel 47. In this embodiment, the sensor(s) detect a change in pressure, but this method is applicable to other types of sensors known in the art. The step of block 204 is now described in more detail with reference to sub-steps of blocks 206-230.

The controller 74 is configured to receive a signal indicative of the fluid metric (e.g., pressure level) in the aspiration channel 47 from the sensor 70 (block 206). The controller 74 is configured to detect a rate of change of the fluid metric (e.g., pressure level) in the aspiration channel 47 responsively to the received signal (block 208). At a decision block 210, the controller 74 is configured to determine if the rate of change passes (e.g., exceeds) a given rate of change. If the rate of change does not pass (e.g., exceed) the given rate of change (branch 212), the method returns to the sub-step of block 206. If the rate of change passes (e.g., exceeds) the given rate of change (branch 214), the controller 74 is configured to reduce the fluid connectivity (block 216) between the inlet port 66-1 and the outlet port 62-1. The sub-step of block 216 may include the controller 74 being configured to apply a current to the solenoid coil 80 to activate the solenoid coil 80 with an opposite polarity to cause the plunger 82 to move and be maintained in the position 92 (block 218). The solenoid valve 64 is closed and kept closed thereby blocking fluid connectivity in the aspiration channel 47 at the location of the plunger 82 thereby isolating the eye from the aspiration tubing line 46 (FIG. 1) and protecting the eye from a vacuum surge.

In some embodiments, rather than the solenoid valve 64 closing completely and fast, the solenoid valve 64 may be controlled to close partially and/or slowly. In some embodiments, the activation of the solenoid valve 64 may also be controlled according to pressure, flow, temperature, or a combination of these type of sensed parameters.

The controller 74 is configured to reduce the vacuum in the aspiration tubing line 46 (block 220) (and the portion of the aspiration channel 47 between the solenoid valve 64 and the aspiration tubing line 46), for example, by reducing the action of the pumping sub-system 26, or opening a vent in the aspiration tubing line 46 or in the aspiration channel 47. The controller 74 is configured to detect the fluid metric (e.g., pressure level) in the aspiration channel 47 responsively to signal received from the sensor 70 (block 222). At a decision block 224, the controller 74 is configured to determine if the fluid metric (e.g., pressure level) passes (e.g., exceeds) a given value (e.g., given pressure level). If fluid metric (e.g., pressure level) does not pass (e.g., exceed) the given value (e.g., given pressure level) (branch 226), the sub-step of block 220 is repeated. If the fluid metric (e.g., pressure level) passes (e.g., exceeds) the given value (e.g., given pressure level) (branch 228), the controller 74 is configured to increase (block 230) the fluid connectivity between the inlet port 66-1 and the outlet port 62-1 responsively to the fluid metric (e.g., pressure level) passing (e.g., exceeding) a given value (e.g., given pressure level), for example, the step of block 202 is repeated.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. An ophthalmic fluid dynamics system, comprising:
a solenoid valve comprising:
    a valve body comprising ports including an inlet port and an outlet port, a valve cavity having a direction of elongation and configured to provide fluid connectivity between respective ones of the ports, a first shock absorber, and a second shock absorber;
    a solenoid coil disposed in the valve body around the valve cavity; and
    a plunger comprising a permanent magnet, and configured to move back- and-forth along the direction of elongation between a first position and a second position in the valve cavity to selectively control the fluid connectivity between respective ones of the ports, wherein the first shock absorber and second shock absorbers are configured to soften striking of the plunger against the valve body in the direction of elongation when the plunger strikes the valve body at the first position, and when the plunger strikes the valve body at the second position respectively; and
    a controller configured to apply at least one current to the solenoid coil to selectively move the plunger between the first position and the second position, and to selectively maintain the plunger in the first position and the second position.

2. The ophthalmic system according to claim 1, wherein the plunger does not have a fixed rest position in the valve cavity.

3. The ophthalmic system according to claim 1, wherein the plunger does not include a restoring element configured to restore the plunger to a fixed rest position.

4. The ophthalmic system according to claim 1, wherein the plunger will not remain in the first position and second position without applying the at least one current to the solenoid coil.

5. The ophthalmic system according to claim 1, wherein the plunger will remain in the first position or the second position upon application of the at least one current to the solenoid coil.

6. The ophthalmic system according to claim 1, wherein the first shock absorber and the second shock absorber do not include a spring.

7. The ophthalmic system according to claim 6, wherein the first shock absorber and the second shock absorber each comprise resilient material.

8. The ophthalmic system according to claim 7, wherein the resilient material comprises one or more selected from the group consisting of silicone rubber, synthetic rubber, natural rubber, and polyurethane.

9. The ophthalmic system according to claim 1, wherein the first shock absorber and the second shock absorber each include a flat surface facing the plunger.

10. The ophthalmic system according to claim 1, wherein the first shock absorber and the second shock absorber each include a rounded surface facing the plunger.

11. The ophthalmic system according to claim 1, wherein the first shock absorber and the second shock absorber each include a conical surface facing the plunger.

12. The ophthalmic system according to claim 1, wherein the controller is configured to:
    apply a first current to the solenoid coil to activate the solenoid coil with a first polarity to cause the plunger to move and be maintained in the first position; and
    apply a second current to the solenoid coil to activate the solenoid coil with a second opposite polarity to cause the plunger to move and be maintained in the second position.

13. The ophthalmic system according to claim 1, wherein:
    the permanent magnet has a center with respect to the direction of elongation;
    the solenoid coil has a center with respect to the direction of elongation; and
    the valve body further comprises a spacer coupled with the first shock absorber, to prevent the center of the magnet from moving in the direction of elongation past the center of the solenoid coil and maintain asymmetry between the center of the solenoid coil and the center of the permanent magnet with respect to the direction of elongation.

14. The ophthalmic system according to claim 13, wherein in the first position of the plunger, the plunger abuts the first shock absorber.

15. The ophthalmic system according to claim 1, further comprising a medical tool including the solenoid valve, an irrigation channel, an aspiration channel which traverses the solenoid valve, and a sensor configured to provide a signal indicative of a fluid metric in the aspiration channel, the controller being configured to selectively control the fluid connectivity in the aspiration channel between the inlet port and the outlet port responsively to the fluid metric.

16. The ophthalmic system according to claim 15, wherein the fluid metric is a pressure level.

17. The ophthalmic system according to claim 15, wherein the controller is configured to detect a rate of change of the fluid metric in the aspiration channel, and reduce the fluid connectivity between the inlet port and the outlet port responsively to the detected rate of change passing a given rate of change.

18. The ophthalmic system according to claim 17, wherein the controller is configured to increase the fluid connectivity between the inlet port and the outlet port responsively to the fluid metric passing a given value.

19. The ophthalmic system according to claim 15, wherein the medical tool further comprises:
    a probe body comprising a horn, a needle, a part of the irrigation channel and a section of the aspiration channel; and
    a fluid dynamics cartridge configured to be reversibly connected to the probe body, and comprising the sensor and the solenoid valve, which comprises another section of the aspiration channel.

20. The ophthalmic system according to claim 19, wherein the fluid dynamics cartridge comprises the controller.

21. An ophthalmic fluid dynamics system, comprising a solenoid valve including:
    a valve body comprising ports including an inlet port and an outlet port, a valve cavity having a direction of elongation and configured to provide fluid connectivity between respective ones of the ports;
    a solenoid coil disposed in the valve body around the valve cavity; and a plunger comprising magnetic material, and configured to move back-and-forth along the direction of elongation between a first position and a second position in the valve cavity to selectively control the fluid connectivity between respective ones of the ports, wherein the valve body includes a first shock absorber and a second shock absorber configured to soften striking of the plunger against the valve body in the direction of elongation when the plunger strikes the valve body at the first position, and when the plunger strikes the valve body at the second position, respectively, and wherein the at least one shock absorber includes a conical surface facing the plunger.

22. The ophthalmic system according to claim 21, wherein the plunger does not have a fixed rest position in the valve cavity.

23. The ophthalmic system according to claim 21, wherein the plunger does not include a restoring element configured to restore the plunger to a fixed rest position.

24. The ophthalmic system according to claim 21, wherein the plunger will not remain in the first position and second position without applying at least one current to the solenoid coil.

25. The ophthalmic system according to claim 21, wherein the plunger will remain in the first position or the second position upon application of at least one current to the solenoid coil.

26. The ophthalmic system according to claim 21, wherein the first shock absorber and the second shock absorber do not include a spring.

27. The ophthalmic system according to claim 26, wherein the first shock absorber and the second shock absorber each comprise resilient material.

28. The ophthalmic system according to claim 27, wherein the resilient material comprises one or more selected from the group consisting of silicone rubber, synthetic rubber, natural rubber, and polyurethane.

* * * * *